United States Patent [19]

Blank et al.

[11] Patent Number: 4,717,514

[45] Date of Patent: Jan. 5, 1988

[54] PROCESS FOR PREPARING P-TOLUIDINE-2-SULPHONIC ACID

[75] Inventors: Heinz U. Blank, Odenthal; Herbert Emde, Cologne; Rolf Schimpf, Leverkusen, all of Fed. Rep. of Germany

[73] Assignee: Bayer Aktiengesellschaft, Leverkusen, Fed. Rep. of Germany

[21] Appl. No.: 848,357

[22] Filed: Apr. 4, 1986

Related U.S. Application Data

[63] Continuation of Ser. No. 692,604, Jan. 17, 1985, abandoned.

[30] Foreign Application Priority Data

Jan. 18, 1984 [DE] Fed. Rep. of Germany ....... 3401572

[51] Int. Cl.$^4$ .......................................... C07C 143/58
[52] U.S. Cl. .................................................. 260/508
[58] Field of Search ......................................... 260/508

[56] References Cited

PUBLICATIONS

Muramoto et al., J. Chem. Soc. of Japan, 1975, pp. 1070–1075.
Chien et al., J. of the Chinese Chem. Soc., vol. 4, 355 (1936).
Liebigs Annalen der Chemie, Band 265, 1891, Seiten 67–87, Weinheim, DE; A. Claus et al.: "Über die Orientirungsfolge bei der Substitution mehrfach substituirter Benzolderivate" Seiten 82–83.

*Primary Examiner*—Nicky Chan
*Attorney, Agent, or Firm*—Sprung Horn Kramer & Woods

[57] ABSTRACT

P-Toluidine-2-sulphonic acid (5-amino-2-methylbenzenesulphonic acid) is obtained in very pure form and virtually free of p-toluidine-3-sulphonic acid (2-amino-5-methylbenzenesulphonic acid) by reacting p-toluidine at 10°–55° C. with oleum in sulphuric acid. The molar ratio of $SO_3$ to p-toluidine in this reaction is 1–3.0:1. The reaction mixture is worked up by pouring into water and filtering off the precipitated p-toluidine-2-sulphonic acid.

14 Claims, No Drawings

PROCESS FOR PREPARING P-TOLUIDINE-2-SULPHONIC ACID

This is a continuation of application Ser. No. 692,604, filed Jan. 17, 1985, now abandoned.

The present invention relates to a process for preparing p-toluidine-2-sulphonic acid (5-amino-2-methylbenzenesulphonic acid), hereinafter referred to in short as p-toluidine-2-acid, by reacting p-toluidine with oleum in sulphuric acid.

p-Toluidine-2-acid can be prepared by sulphonating p-nitrotoluene with fuming sulphuric acid (Ann. 155, 1 (1870); Rec. Trav. Chim. Pays-Bas 29, 368 (1910)) or with $SO_3$ (GB 1,164,752) and then reducing the nitro group, for example with iron powder (BIOS Reports 1153, page 174).

Aminoarylsulphonic acids can also be prepared from the corresponding acid anilinium sulphates by the so-called "baking process" (Helv. Chem. Acta 15, 1372 (1932)); however, in this process the sulphonic acid group is substituted into the p-position relative to the amino group or, if the p-position is occupied, into the o-position relative to the amino group. In this way p-toluidine is converted into 2-amino-5-methylbenzenesulphonic acid (hereinafter referred to as p-toluidine-3-acid).

It has also already been reported to react p-toluidine with twice the weight of strongly fuming $H_2SO_4$ containing 50% of $SO_3$, but in this form of the reaction the formation of desired p-toluidine-2-acid is always accompanied by the formation of significant amounts of unwanted p-toluidine-3-acid. The 3-acid has to be washed out first with water and the residue has to be then recrystallized from hot water to give an unspecified yield of 2-acid of unspecified purity (Ann. 265, 67 (1891)).

Later repeats of the work described in the preceding paragraph confirm the unwanted 3-acid content. For instance, in J. Chem. Soc. of Japan, 1975, pages 1070–1075, the sulphonation is carried out by introducing p-toluidine into 7 times the amount by weight of 20% strength oleum with no added solvents or diluents and working up the reaction product into the potassium salt by way of the barium salt. NMR spectroscopy showed that the most favourable mixing ratio of 74% of desired 2-acid and 26% of unwanted acid was obtained when the reaction temperature was held at 20° C. As the reaction temperature rises the proportion of 2-acid decreases and that of the 3-acid increases. According to Table 4 on page 1,073 of J. Chem. Soc. of Japan 1975, the isolated yield of potassium salt at the most favourable ratio of 2-acid to 3-acid is only 13%.

J. of the Chinese Chem. Soc., Vol. 4, 355 (1936) is a repeat of the method of Ann. 265, 67 (1891) but with a larger amount of oleum and the reaction temperature being restricted to less than 10° C. In this case too, the resulting 2-acid is contaminated with an unspecified amount of 3-acid which can only be removed by repeatedly washing with alcohol and recrystallising from water, during which operations yield losses are unavoidable.

It has now been found, surprisingly, that, on moving to smaller $SO_3$/p-toluidine and smaller $H_2SO_4$/p-toluidine ratios, the proportion of resulting 3-acid even at medium temperatures can be reduced to such an extent as to produce, if the working-up method described below is compiled with, a 2-acid in high yield which is virtually free of 3-acid.

The invention accordingly provides a process for preparing p-toluidine-2-sulphonic acid by reacting $SO_3$-containing sulphuric acid (oleum) with p-toluidine dissolved in sulphuric acid, which is characterised in that 1.5–10 moles of sulphuric acid are used to dissolve each mole of p-toluidine and sufficient oleum is added at 10°–55° C. to the solution that 1–3 moles of free $SO_3$ are present per mole of p-toluidine.

According to the invention the p-toluidine is used in the form of a solution in sulphuric acid. In this solution, 1.5–10 moles of $H_2SO_4$, preferably 1.7–8 moles of $H_2SO_4$, are present per mole of p-toluidine. The $H_2SO_4$ used for this purpose will generally be of 100% strength (the so-called monohydrate form). However, it is also possible to use sulphuric acids having a low water content, for example a water content of up to 8, preferably up to 5, % of $H_2O$, relative to the total amount of acid. This water will, of course, use up a portion of the $SO_3$ to be added later in the form of oleum, so that the amount of this $SO_3$ may have to be increased in line with the water content. The p-toluidine can be added in solid form, for example in the form of a powder, or in liquid form, as a melt. The temperature at the time the p-toluidine is added to the sulphuric acid has no effect on the subsequent course of the reaction. If the temperature rises beyond the temperature range which, according to the invention, should prevail at the time the oleum is added, the p-toluidine solution in sulphuric acid must be cooled by an appropriate amount before the oleum is added. It is therefore advisable to maintain the temperature at which the p-toluidine is added to $H_2SO_4$ in the range within which the subsequent addition of oleum is to take place.

The free $SO_3$ content in the oleum is advantageously 20–65% by weight; the oleum used preferably has an $SO_3$ content of 60–65% by weight.

According to the invention, sufficient oleum is added to the p-toluidine dissolved in $H_2SO_4$ as to ensure that 1–3 moles, preferably 1.1–2.5 moles, particularly preferably 1.2–2 moles and very particularly preferably 1.3–1.8 moles of $SO_3$ are present per mole of p-toluidine. According to the invention, the temperature at the time the oleum is added should be 10°–55° C., preferably 15°–50° C. and particularly preferably 20°–45° C. If the addition of oleum is commenced in the lower part of the specified temperature range, it is possible to raise the temperature during the addition of the oleum into the upper part of the specified temperature range, if desired in more than one step.

Once the oleum has been added, the reaction mixture can be subjected, in addition, to a secondary reaction, in particular if major amounts of p-toluidine are still present. The presence of p-toluidine which has not yet reacted can be determined, for example, by thin layer chromatography on a sample of the reaction mixture. The secondary reaction can be carried out within said range from 10° to 55° C. However, it is also admissible to carry out the secondary reaction within the range 55°–80° C. In the case where this temperature of 55°–80° C. is used for the secondary reaction, the reaction mixture is not adjusted to this temperature until at least 50% of the total oleum has been added, preferably not until all the oleum has been added, so that, if desired, at least 50% of the total oleum is added at 10°–55° C. and the remainder is added at 55°–80° C. During the secondary reaction the temperature can again be raised in more than one step within the specified temperature range 10°–55° C. or, if desired, 55°–80° C.

To work up, water is added to the reaction mixture. This water can be in its normal form, in the form of an ice/water mixture, or in the form of crushed ice. Similarly, the reaction mixture can be added to the water in any one of the indicated forms. On addition of the water to the reaction mixture the p-toluidine-2-acid precipitates and can be isolated by customary methods, such as filtering or centrifuging. The amount of water added in one of the indicated forms in the working-up procedure is calculated in such a way as to form in addition to the crystallized p-toluidine-2-acid an aqueous phase of a dilute acid having a sulphuric acid content of 10–60% by weight, preferably 20–50% by weight and very particularly preferably 30–40% by weight, relative to the total aqueous phase.

The secondary reaction can be carried out within said range of 10°–55° C. However, it is also permissible to carry out the secondary reaction within the range from 55° to 80° C.

The p-toluidine-2-acid isolated from the aqueous phase has a purity in respect of the unwanted 3-acid of greater than 99%, especially greater than 99.5%, and in many cases greater than 99.95%. This isomeric purity of the 2-acid obtained was determined by high pressure liquid chromatography (HPLC) where the 2- and the 3-sulphonic acids are differentiated and readily separated by having different retention times. The structures of the p-toluidine-2-sulphonic and -3-sulphonic acids in question were confirmed by elemental analysis and by a thin layer chromatography comparison after diazotisation and coupling with a coupling component. In the light of the literature discussed above, the high selectivity with which p-toluidine-2-acid is prepared in the method according to the invention was not foreseeable. The fact that the desired 2-sulphonic acid is the only product isolated, and without an additional purifying operation such as washing or recrystallizing, is therefore surprising.

p-Toluidine-2-sulphonic acid is used for example in antihelmintic agents for domestic animals (French Patent of Addition No. 84,259), as a diazo component in dyestuffs (Soviet Pat. No. 191,017), as an additive for the formation of crystallizable thermoplastics from polyolefins and nylons (German Offenlegungsschrift No. 2,002,489) and in fluorescent brighteners (Yuki Gosei Kagaku Kyokai Shi 1972, 30, 449).

EXAMPLE 1

107 g (1 mole) of p-toluidine were added at 20°–30° C. a little at a time to 100 ml of 100% strength sulphuric acid in the course of 1½ hours. 221 ml of 20% strength oleum were then added at 20°–30° C. in the course of about 2½ hours, and, when all the oleum had been added, the batch was heated to 65° C. and was held at that temperature for 1 hour. The batch was discharged onto 817 ml of water, whereupon the temperature rose to 80° C. and p-toluidine-2-acid precipitated. The mixture was then cooled down to 20° C., and the precipitated sulphonic acid was filtered off with suction.

The result was 210 g of moist p-toluidine-2-acid having a purity of 80.0%; that corresponds to a yield of 90%, relative to the starting p-toluidine. The p-toluidine content is below 0.1% by weight; the p-toluidine-3-acid content is below the thin layer chromatography detection limit.

EXAMPLE 2

139.2 of p-toluidine (99.5% pure=1.292 moles) melt were added dropwise at room temperature to 640 g of 100% strength sulphuric acid. The temperature was held at 30°–40° C. by cooling with water. The mixture was stirred at 30° C. for 15 minutes after all the toluidine had been added. 224 g of 65% strength oleum were then added dropwise at 30°–40° C. in the course of an hour. The mixture was stirred at 40° C. for 1 hour and at 60° C. for another hour. The sulphonating mixture was discharged without cooling onto 1,160 ml of water and the resulting mixture was then cooled down to 20° C. The suspension was filtered with suction through a glass frit. The crystalline, pale yellow p-toluidine-2-acid had a moist weight of 302.3 g and a p-toluidine-2-acid content of 75.5% by weight.

The yield relative to starting p-toluidine was 94.4%. The p-toluidine-3-acid content was below 0.05% by weight.

What is claimed is:

1. A process for preparing 5-amino-2-methylbenzenesulphonic acid which comprises adding $SO_3$-containing sulphuric acid, said $SO_3$-containing sulphuric acid having a free $SO_3$ content of 60 to 65% by weight and being employed in an amount of 1–3 moles of free $SO_3$ per mole of p-toluidine, to p-toluidine dissolved in 1.5–10 moles of sulphuric acid per mole of p-toluidine, wherein in a first reaction conducted at a temperature of 10° to 55° C. a portion of the total required amount of the $SO_3$-containing sulfuric acid is added to the p-toluidine, said portion being at least 50% of the total required amount of the $SO_3$-containing sulphuric acid, and thereafter conducting a secondary reaction at a temperature of 55° to 80° C. wherein the remaining amount of the required amount of the $SO_3$-containing sulphuric acid is added, and wherein after said secondary reaction, water is added to the reaction mixture, said water added in an amount whereby to form, in addition to crystallized 5-amino-2-methylbenzenesulfonic acid, an aqueous phase of a dilute acid having a sulphuric acid content of 10 to 60% by weight, relative to the total aqueous phase.

2. A process according to claim 1 wherein said p-toluidine is dissolved in 1.7–8 moles of sulphuric acid.

3. A process according to claim 1 wherein 1.1–2.5 moles of free $SO_3$ are employed per mole of p-toluidine.

4. A process according to claim 1 wherein 1.2–2 moles of free $SO_3$ are employed per mole p-toluidine.

5. A process according to claim 1 wherein said $SO_3$-containing sulphuric acid is added to said p-toluidine at 15°–50° C. in said first reaction.

6. A process according to claim 1 wherein said $SO_3$-containing sulphuric acid is added to said p-toluidine at 20°–45° C. in said first reaction.

7. A process according to claim 1 wherein the temperature is increased in more than one step to attain the temperature of the secondary reaction.

8. A process according to claim 1, wherein the sulphuric acid for dissolving the p-toluidine is 100% strength.

9. A process according to claim 1, wherein the sulphuric acid for dissolving the p-toluidine has a water content up to 8% water.

10. A process according to claim 1, wherein the sulphuric acid for dissolving the p-toluidine has a water content up to 5% water. 1

11. A process according to claim 1, wherein 1.3 to 1.8 moles of free $SO_3$ are employed per mole of p-toluidine.

12. A process according to claim 1, wherein the sulphuric acid content of the aqueous phase of the dilute acid is 20 to 50% by weight.

13. A process according to claim 1, wherein the sulphuric acid content of the aqueous phase of the dilute acid is 30 to 40% by weight.

14. A process according to claim 1, wherein the sulphuric acid content of the aqueous phase of the dilute acid is 20 to 40% by weight.

* * * * *